United States Patent
Yamano et al.

(10) Patent No.: US 8,481,461 B2
(45) Date of Patent: Jul. 9, 2013

(54) DETECTION METHOD FOR MICROARRAY

(75) Inventors: Hirofumi Yamano, Yamaguchi (JP);
Koichi Hirayama, Yamaguchi (JP);
Akane Ito, Yamaguchi (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 13/520,372

(22) PCT Filed: Dec. 13, 2010

(86) PCT No.: PCT/JP2010/072321
§ 371 (c)(1),
(2), (4) Date: Jul. 3, 2012

(87) PCT Pub. No.: WO2011/081012
PCT Pub. Date: Jul. 7, 2011

(65) Prior Publication Data
US 2012/0289427 A1    Nov. 15, 2012

(30) Foreign Application Priority Data
Jan. 4, 2010  (JP) .................................. 2010-000251

(51) Int. Cl.
*C40B 30/04* (2006.01)
*C12Q 1/68* (2006.01)
*C12M 1/34* (2006.01)

(52) U.S. Cl.
USPC ............................ 506/9; 435/6.1; 435/287.1

(58) Field of Classification Search
USPC ................................................ 506/9; 435/6.1
See application file for complete search history.

(56) References Cited

U.S. PATENT DOCUMENTS

| | | | |
|---|---|---|---|
| 2003/0198952 A9 | 10/2003 | Okamoto et al. | |
| 2004/0132080 A1 | 7/2004 | Kawaguchi et al. | |
| 2008/0293581 A1* | 11/2008 | Rogler et al. | 506/9 |
| 2009/0093373 A1 | 4/2009 | Kawaguchi et al. | |

FOREIGN PATENT DOCUMENTS

| | | | |
|---|---|---|---|
| JP | 2004-28695 | | 1/2004 |
| JP | 2006-029953 | | 2/2006 |
| JP | 2006029953 A | * | 2/2006 |
| JP | 3880361 | | 2/2007 |
| JP | 4261661 | | 2/2009 |
| JP | 2009-236626 | | 10/2009 |
| JP | 2009236626 A | * | 10/2009 |

OTHER PUBLICATIONS

Hwang et al., "Quantitative oligonucleotide microarray data analysis with an artificial standard probe strategy," Biosens. Bioelectron. 2008, 23:1738-1744.*

* cited by examiner

Primary Examiner — Samuel Woolwine
Assistant Examiner — Kaijiang Zhang
(74) Attorney, Agent, or Firm — McCarter & English

(57) ABSTRACT

Described is a means for objectively determining hybridization failure in addition to performance degradation, insufficient washing and the like in a microarray. In particular a method for detecting the hybridization between a probe polynucleotide and a target polynucleotide by using a microarray is presented.

9 Claims, 9 Drawing Sheets

Probe mixture 5μM →
Probe mixture 20μM →
No probe →
O type probe alone 10μM →
B type probe alone 10μM →

← Probe mixture 2.5μM
← Probe mixture 10μM
← Probe mixture 40μM
← AB type probe alone 10μM
← AO type probe alone 10μM

SEQUENCE LISTING

<160> NUMBER OF SEQ ID NOS: 27

<210> SEQ ID NO 1
<211> LENGTH: 20
<212> TYPE: DNA
<213> ORGANISM: Artificial
<220> FEATURE:
<223> OTHER INFORMATION: Synthetic DNA

<400> SEQUENCE: 1
tcctcgtggt gaccccttgg                                       20

<210> SEQ ID NO 2
<211> LENGTH: 20
<212> TYPE: DNA
<213> ORGANISM: Artificial
<220> FEATURE:
<223> OTHER INFORMATION: Synthetic DNA

<400> SEQUENCE: 2
tcctcgtggt accccttggc                                       20

<210> SEQ ID NO 3
<211> LENGTH: 20
<212> TYPE: DNA
<213> ORGANISM: Artificial
<220> FEATURE:
<223> OTHER INFORMATION: Synthetic DNA

<400> SEQUENCE: 3
acaagtacct gctgcgccac                                       20

<210> SEQ ID NO 4
<211> LENGTH: 20
<212> TYPE: DNA
<213> ORGANISM: Artificial
<220> FEATURE:
<223> OTHER INFORMATION: Synthetic DNA

<400> SEQUENCE: 4
acaagtacct actgcgccac                                       20

<210> SEQ ID NO 5
<211> LENGTH: 20
<212> TYPE: DNA
<213> ORGANISM: Artificial
<220> FEATURE:

<223> OTHER INFORMATION: Synthetic DNA

<400> SEQUENCE: 5
agctcagctt gctgtgtgtt                                               20

<210> SEQ ID NO 6
<211> LENGTH: 19
<212> TYPE: DNA
<213> ORGANISM: Artificial
<220> FEATURE:
<223> OTHER INFORMATION: Synthetic DNA

<400> SEQUENCE: 6
agatgctgca tgaatgacc                                                19

<210> SEQ ID NO 7
<211> LENGTH: 20
<212> TYPE: DNA
<213> ORGANISM: Artificial
<220> FEATURE:
<223> OTHER INFORMATION: Synthetic DNA

<400> SEQUENCE: 7
gcctgccttg cagatacgtg                                               20

<210> SEQ ID NO 8
<211> LENGTH: 20
<212> TYPE: DNA
<213> ORGANISM: Artificial
<220> FEATURE:
<223> OTHER INFORMATION: Synthetic DNA

<400> SEQUENCE: 8
cagagtttac ccgttctgct                                               20

<210> SEQ ID NO 9
<211> LENGTH: 19
<212> TYPE: DNA
<213> ORGANISM: Artificial
<220> FEATURE:
<223> OTHER INFORMATION: Synthetic DNA

<400> SEQUENCE: 9
cccaatttaa atgaggacc                                                19

<210> SEQ ID NO 10
<211> LENGTH: 19
<212> TYPE: DNA
<213> ORGANISM: Artificial
<220> FEATURE:
<223> OTHER INFORMATION: Synthetic DNA

<400> SEQUENCE: 10
cccaatttga atgaggacc                                                19

<210> SEQ ID NO 11
<211> LENGTH: 19
<212> TYPE: DNA
<213> ORGANISM: Artificial
<220> FEATURE:
<223> OTHER INFORMATION: Synthetic DNA

<400> SEQUENCE: 11
cccaacctaa atgaggacc                                                19

<210> SEQ ID NO 12

```
<211> LENGTH: 19
<212> TYPE: DNA
<213> ORGANISM: Artificial
<220> FEATURE:
<223> OTHER INFORMATION: Synthetic DNA

<400> SEQUENCE: 12
cctaatttga atgaggatc                                                19

<210> SEQ ID NO 13
<211> LENGTH: 20
<212> TYPE: DNA
<213> ORGANISM: Artificial
<220> FEATURE:
<223> OTHER INFORMATION: Synthetic DNA

<400> SEQUENCE: 13
gctgtaactg tacaaacaga                                               20

<210> SEQ ID NO 14
<211> LENGTH: 20
<212> TYPE: DNA
<213> ORGANISM: Artificial
<220> FEATURE:
<223> OTHER INFORMATION: Synthetic DNA

<400> SEQUENCE: 14
gctgtaacag tacaaacaga                                               20

<210> SEQ ID NO 15
<211> LENGTH: 20
<212> TYPE: DNA
<213> ORGANISM: Artificial
<220> FEATURE:
<223> OTHER INFORMATION: Synthetic DNA

<400> SEQUENCE: 15
gctgtaactg taaaaacaga                                               20

<210> SEQ ID NO 16
<211> LENGTH: 20
<212> TYPE: DNA
<213> ORGANISM: Artificial
<220> FEATURE:
<223> OTHER INFORMATION: Synthetic DNA

<400> SEQUENCE: 16
gctgtgactg taaaaacaga                                               20

<210> SEQ ID NO 17
<211> LENGTH: 20
<212> TYPE: DNA
<213> ORGANISM: Artificial
<220> FEATURE:
<223> OTHER INFORMATION: Synthetic DNA

<400> SEQUENCE: 17
aacagaggtt attggaataa                                               20

<210> SEQ ID NO 18
<211> LENGTH: 20
<212> TYPE: DNA
<213> ORGANISM: Artificial
<220> FEATURE:
<223> OTHER INFORMATION: Synthetic DNA

<400> SEQUENCE: 18
```
aacagaggtc attggaataa                                              20

<210> SEQ ID NO 19
<211> LENGTH: 20
<212> TYPE: DNA
<213> ORGANISM: Artificial
<220> FEATURE:
<223> OTHER INFORMATION: Synthetic DNA

<400> SEQUENCE: 19
aacagaggtt atgggaataa                                              20

<210> SEQ ID NO 20
<211> LENGTH: 20
<212> TYPE: DNA
<213> ORGANISM: Artificial
<220> FEATURE:
<223> OTHER INFORMATION: Synthetic DNA

<400> SEQUENCE: 20
ctggggtaga tgctattaca                                              20

<210> SEQ ID NO 21
<211> LENGTH: 20
<212> TYPE: DNA
<213> ORGANISM: Artificial
<220> FEATURE:
<223> OTHER INFORMATION: Synthetic DNA

<400> SEQUENCE: 21
ctggggtaga tgctataaca                                              20

<210> SEQ ID NO 22
<211> LENGTH: 20
<212> TYPE: DNA
<213> ORGANISM: Artificial
<220> FEATURE:
<223> OTHER INFORMATION: Synthetic DNA

<400> SEQUENCE: 22
ctgggctaga tgctataaca                                              20

<210> SEQ ID NO 23
<211> LENGTH: 20
<212> TYPE: DNA
<213> ORGANISM: Artificial
<220> FEATURE:
<223> OTHER INFORMATION: Synthetic DNA

<400> SEQUENCE: 23
atgcttccta aacccagaaa                                              20

<210> SEQ ID NO 24
<211> LENGTH: 20
<212> TYPE: DNA
<213> ORGANISM: Artificial
<220> FEATURE:
<223> OTHER INFORMATION: Synthetic DNA

<400> SEQUENCE: 24
atgctttcta aacccagaaa                                              20

<210> SEQ ID NO 25
<211> LENGTH: 20
<212> TYPE: DNA
<213> ORGANISM: Artificial
<220> FEATURE:

```
<223> OTHER INFORMATION: Synthetic DNA

<400> SEQUENCE: 25
atgctttcta aatccagaaa                                                   20

<210> SEQ ID NO 26
<211> LENGTH: 20
<212> TYPE: DNA
<213> ORGANISM: Artificial
<220> FEATURE:
<223> OTHER INFORMATION: Synthetic DNA

<400> SEQUENCE: 26
caagtgccaa aactactaat                                                   20

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
tgcatgaagg ttaagcatgc                                                   20
```

DETECTION METHOD FOR MICROARRAY

RELATED APPLICATIONS

This application is a national stage application filed under 35 USC §371 of PCT/JP2010/072321, filed Dec. 13, 2010, which claims the benefit of Japanese Patent Application No. 2010-000251, filed Jan. 4, 2010, both of which are incorporated herein, in entirety, by reference.

TECHNICAL FIELD

The present invention relates to a method for detecting the hybridization between a probe polynucleotide and a target polynucleotide by using a microarray.

BACKGROUND ART

Attempts have been made to not only clarify gene structures of a wide variety of organisms but also elucidate gene functions at a genomic level. Also, technique for efficiently analyzing gene function has been rapidly developed. A microarray refers to an array prepared by highly densely aligning and immobilizing a number of polynucleotides in every predetermined region on a carrier such as a slide glass and is very usefully used for determining the nucleotide sequence of a gene and simultaneously analyzing e.g., gene expression, mutation and polymorphism. Analysis for genetic information using the microarray is extremely useful for e.g., studies for drug development, disease diagnosis and development of preventive methods.

In the detection using a microarray, first, a target polynucleotide labeled with a radioactive isotope or a fluorescence dye is hybridized with probe polynucleotides highly densely aligned on the surface of a carrier. The target polynucleotide, which has a complementary nucleotide sequence to the probe polynucleotide, complementarily hybridizes with the probe polynucleotide; however, a polynucleotide failed to hybridize is removed by washing.

In the detection of hybridization using a microarray, a decision error may occur due to performance degradation, insufficient washing or the like in each microarray. However, whether the decision is error or not is determined at the discretion of the user who operates the microarray and thus quite ambiguous. In the circumstances, it has been impossible to process a large number of samples in an automatic apparatus constituted of a detector and a reactor in combination.

In the method described in Patent Document 1, to eliminate a decision error that occurs when the brightness of a spot is equal to or lower than a lower detection limit of a detector, or equal to or higher than an upper detection limit thereof, a microarray spotted with probe DNAs different in concentration is used and determination is made only based on the results from spots having brightness within a predetermined range. However, in this method, performance degradation, insufficient washing and the like in each microarray cannot be detected.

In the method described in Patent Document 2, a marker substance is covalently bonded to a probe array and the position of a spot of each probe is rapidly and accurately specified based on the position of the marker substance. However, in the method, performance degradation, insufficient washing and the like in each probe array can be detected; however, the occurrence of hybridization failure and PCR failure cannot be detected.

CITATION LIST

Patent Document
  Patent Document 1: JP Patent No. 0880361
  Patent Document 2: JP Patent No. 4261661

SUMMARY OF INVENTION

Technical Problem

An object of the present invention is to provide means for objectively determining performance degradation, insufficient washing and the like in each microarray as well as hybridization failure and a defective target polynucleotide and means for positioning of spots.

Solution to Problem

The present inventors employed a microarray having, in addition to detection spots in which a plurality of types of probe polynucleotides are each immobilized, a reference spot in which at least two types of probe polynucleotides immobilized in the detection spots are immobilized. Then, a fluorescent labeled target polynucleotide was brought into contact with the microarray and a hybridization reaction is caused to proceed. As a result, they found that not only the positions of detection spots but also reliability of each microarray and reliability of the hybridization reaction can be determined first by measuring the fluorescence of the reference spot, and accomplished the invention.

More specifically, the present invention includes the following inventions.

(1) A method for detecting the hybridization between a probe polynucleotide and a target polynucleotide by using a microarray, including
  1) a step of bringing a fluorescent labeled target polynucleotide into contact with a microarray having a plurality of detection spots in which a plurality of types of probe polynucleotides are each immobilized and at least one reference spot in which at least two types of probe polynucleotides immobilized in the detection spots are immobilized,
  2) a step of removing an unreacted target polynucleotide by washing the microarray,
  3) a step of measuring fluorescence of the reference spot and determining that if a predetermined value is satisfied, measurement can be made, and
  4) a step of measuring fluorescence of each of the detection spots in which the probe polynucleotides are immobilized, if it is determined that measurement can be made.

(2) The method according to item (1), in which all types of probe polynucleotides immobilized in the detection spots are immobilized in the reference spot.

(3) The method according to item (1) or (2), in which the target polynucleotide to be brought into contact with the microarray inevitably contains the polynucleotide to be hybridized with the probe polynucleotides immobilized in the reference spot.

(4) The method according to any one of items (1) to (3), in which, the detection spots and the reference spots are aligned in the microarray; at least two reference spots are present; and a line connecting any two of the reference spots is defined as a base line, the positions of the detection spots are detected based on the distance from the reference spots and the angle with the base line.

(5) The method according to item (4), in which the detection spots and the reference spots are arranged in the form of a lattice whose outer periphery forms a tetragon and the reference spots are present at different apexes of the tetragon.

(6) The method according to any one of items (1) to (5), in which, the detection spots and the reference spots are aligned in the microarray in the form of a lattice whose outer periphery forms a square or a rectangle; the reference spots are present at two apexes of a diagonal line thereof; and the intersection point at which two linear lines passing through the reference spots intersect at right angles is detected, the lengths of the two connection lines connecting the intersection point and the reference spots are detected to detect the position of each of the detection spots on the connection line based on the length of the connection line and the number of spots.

(7) The method according to any one of items (1) to (6), in which, a marker polynucleotide has a homology of 95% or more with a polynucleotide complementary to any of the probe polynucleotides immobilized in the detection spots.

(8) A kit for detecting the hybridization between a probe polynucleotide and a target polynucleotide, including a microarray having a plurality of detection spots in which a plurality of types of probe polynucleotides are each immobilized and at least one reference spot in which at least two types of probe polynucleotides immobilized in the detection spots are immobilized; and a fluorescent labeled marker polynucleotide capable of hybridizing with any of the probe polynucleotides immobilized in the detection spots.

(9) The kit according to item (8), in which all types of probe polynucleotides immobilized in the detection spots are immobilized in the reference spot.

The specification includes the contents described in the specification and/or drawings of JP Patent Application No. 2010-000251 based on which the priority of the present application is claimed.

Advantageous Effects Of Invention

The present invention enables to determine reliability of each microarray and carry out measurement by using a reliable microarray. Furthermore, the reliability of a hybridization reaction can be determined. Accordingly, a decision error can be suppressed. Moreover, if it is used in combination with an automatic reactor, etc., microarray measurement can be automatically carried out with high reliability. In addition, a reference spot can be detected without adding an additional reagent to a sample. Also in this point, the present invention is advantageous.

DESCRIPTION OF EMBODIMENTS

Figure 1:
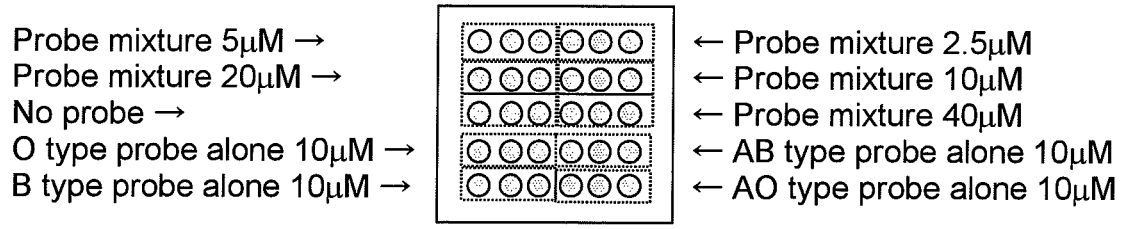
FIG. 1 shows an embodiment of arrangement of probe DNA spots (detection spots) and probe DNA mixture spots (reference spots) in a microarray.

The present invention relates to a method for detecting the hybridization between a probe polynucleotide and a target polynucleotide by using a microarray.

In the present invention, the polynucleotide includes an oligonucleotide and a nucleic acid including DNA and RNA. The DNA includes a single stranded DNA and a double stranded DNA. Furthermore, the nucleic acid includes artificial nucleic acids having a modified phosphoric diester site; artificial nucleic acids having a furanose site with a modified glycosyl bond and a modified hydroxyl group; artificial nucleic acids having a modified nucleobase; and artificial nucleic acids having a structure other than a sugar-phosphoric acid skeleton. Specific examples thereof include an artificial nucleic acid obtained by substituting an oxygen atom at the phosphate site with a sulfur atom, such as a phospholothioate type, phospholodithioate type, phospholodiamidate type, methylphosphonate type or methylphosphonothioate type artificial nucleic acids; an artificial nucleic acid having a modified substituent on a furanose ring, a pyranose type artificial nucleic acid having a sugar ring skeleton to which a single carbon atom is added or a polycyclic sugar skeleton type artificial nucleic acid; and a pyrimidine C-5 position modified base type, a purine C-7 position modified base type or a ring extension modification base type artificial nucleic acid.

In the present invention, the "probe polynucleotide", which has the same meaning as usually used in the art, refers to a polynucleotide for use in detecting a desired gene and specifically hybridizing with a polynucleotide or a fragment thereof corresponding to the desired gene. As the probe polynucleotide, e.g., usually, a synthetic oligonucleotide, cDNA and genomic DNA and fragments of these as well as modified ones of these (for example, a double strand modified from a single strand) are used. The probe polynucleotide has usually 3 to 5000 bases, preferably 10 to 1000 bases and further preferably 15 to 70 bases. The concentration of the probe polynucleotide to be immobilized to a microarray usually falls within the range of 0.2 µM to 50 µM.

In the present invention, the "target polynucleotide", which has the same meaning as usually used in the art, refers to a polynucleotide serving as a detection target. The "target" is sometimes referred to as "hyoteki". Usually, a polynucleotide derived from a test specimen and a polynucleotide enzymatically synthesized or amplified based on the specimen-derived polynucleotide, such as mRNA, cDNA, aRNA and fragments of these as well as modified ones of these are used.

The "hybridize", "hybridization reaction" or "hybridization", which has the same meaning as usually used in the art, refers to forming a double strand between polynucleotides having complementary sequences to each other, for example, between single stranded DNAs, between single stranded RNAs, or between a single stranded DNA and a single stranded RNA, under appropriate conditions. In the present invention, hybridization is preferably carried out under stringent conditions.

In the present invention, a fluorescent labeled target polynucleotide is used. A labeling method and the type of label are not particularly limited as long as the hybridization between a probe polynucleotide and a target polynucleotide can be detected, and are known in the art. For example, a fluorescent labeled target polynucleotide can be obtained by incorporating a substrate (mostly UTP) covalently bonded with a fluorescent label when synthesizing or amplifying a target polynucleotide. Examples of the fluorescent label include Cy dyes such as Cy3 and Cy5, FITC, RITC, rhodamine, Texas Red, TET, TAMRA, FAM, HEX and ROX.

In the present invention, a microarray having not only a plurality of detection spots in which probe polynucleotides are immobilized but also at least one reference spot, preferably at least two, more preferably 2 to 4 and further preferably 2 reference spots in which at least two types and preferably all types of probe polynucleotides immobilized in the detection spots are immobilized, is used. The concentration of the probe polynucleotides to be immobilized in a reference spot, in total, falls within the range of usually 0.2 µM to 100 µM. It is preferable that the probe polynucleotides to be immobilized in a reference spot are each present in the same concentration and the total concentration of them is preferably the above concentration.

In the present invention, the types of probe polynucleotides to be immobilized in the detection spots of a microarray are two or more, usually, 256 types or less and preferably 64 types or less. In the present invention, since at least two types of probe polynucleotides immobilized in detection spots, preferably all types thereof are immobilized in a reference spot preferably in the same concentration, if the number of types of probe polynucleotides is excessively large, the concentration of a single probe polynucleotide in the reference spot becomes low and the intensity of fluorescence thereof at the reference spot becomes weak.

In the present invention, the target polynucleotide to be brought into contact with a microarray usually inevitably contains a polynucleotide which can hybridize with the probe polynucleotide immobilized in a reference spot. Therefore, when a fluorescent labeled target polynucleotide is brought into contact with a microarray, as long as the microarray has not caused degradation and a detection procedure such as a nucleic acid amplification reaction is normally carried out, a signal is inevitably detected at the reference spot. Furthermore, based on the presence or absence of a signal at the reference spot, reliability of each microarray can be determined. As a result, measurement can be carried out by using a reliable microarray. Also, reliability of a hybridization reaction can be determined and thus a decision error can be suppressed. Furthermore, since the position of a detection spot can be automatically determined based on the position in a reference spot, measurement of the microarray can be made automatically with high reliability in combination with an automatic reactor, etc.

The probe polynucleotides immobilized in detection spots refer to probe polynucleotides virtually used for detection directed by the microarray. The phrase "all types of probe polynucleotides immobilized in the detection spots are immobilized" means that all types of probe polynucleotides to be virtually used for detection directed by the microarray are immobilized. Therefore, even if a polynucleotide, which is not virtually used for detection, is immobilized in a microarray and the polynucleotide is not immobilized in a reference spot, such a case is included in an embodiment in which all types of probe polynucleotides are immobilized.

The embodiment in which all types of probe polynucleotides which are immobilized in detection spots are immobilized, is preferably used in the case where a target polynucleotide includes a polynucleotide inevitably hybridizes with any of the probe polynucleotides immobilized in detection spots of a microarray and the target polynucleotide is identified by detecting to which detection spot the target polynucleotide is hybridized. In other words, this embodiment is preferable where the target polynucleotide to be in contact with a microarray inevitably contains a polynucleotide capable of hybridizing with any of the probe polynucleotides immobilized in detection spots. This is because such a target polynucleotide inevitably hybridizes with any of the probe polynucleotides immobilized in a reference spot, meaning that a signal is detected at a reference spot as long as the microarray has not been degraded and a detection procedure such as a nucleic acid amplification reaction has been normally carried out. In addition, based on the presence or absence of a signal at a reference spot, the reliability of each microarray can be determined and measurement can be performed by using a reliable microarray. Furthermore, the reliability of a hybridization reaction can be determined, and a decision error can be suppressed. Moreover, since the position of a detection spot can be automatically determined based on the position of a reference spot, measurement of a microarray can be automatically carried out with a high reliability in combination with an automatic reactor.

Such an embodiment includes a case of using a microarray in which a probe polynucleotide corresponding to a nucleic acid inevitably contained in a biological sample is immobilized, when applying a target nucleotide derived from the biological sample. For example, in case where a nucleic acid derived from a gene inevitably contained in the biological sample, and the gene has a plurality of genome types (polymorphism or mutation), all types of probe polynucleotides corresponding to all the genomic types are each immobilized in the detection spots of a microarray.

More specifically, a case of determining an ABO blood type may be mentioned. In this case, all probe polynucleotides corresponding to polymorphisms of a ABO glycosyl transferase gene (Yamamoto et al., 1990, Nature 345(17): 229-233), respectively, are immobilized separately to detection spots of a microarray, and a target polynucleotide derived from a nucleic acid extracted from human cells, tissues or body fluid such as blood (for example, a target polynucleotide obtained by amplifying an ABO glycosyl transferase gene by using the nucleic acid as a template), is brought into contact with the microarray. In addition, a drug response test and a drug efficacy test according to gene polymorphism determination can be exemplified.

The present invention also includes an aspect where a target polynucleotide does not contain a polynucleotide capable of hybridizing with any of the probe polynucleotides immobilized in detection spots in a microarray. In such a case, a signal is not detected in a reference spot, either. Therefore, first, the fluorescence of a reference spot is detected. If fluorescence does not satisfy a predetermined value, it can be determined that measurement cannot be made. For example, in the case of determining, the hometown of a human by identifying polymorphism of a gene (for example, VP1 gene) in a virus (for example, BK virus), which may possibly be transmitted to a human, a microarray, in which all types of probe polynucleotides corresponding to polymorphism of the virus gene are immobilized, can be used. If a specimen is infected with a virus, fluorescence can be detected in any of the detection spots; at the same time, fluorescence is detected in a reference spot. Therefore, first, fluorescence of a reference spot is measured. Then, only if fluorescence satisfies a predetermined value, fluorescence of the detection spots may be measured. If fluorescence of the reference spot is not detected, measurement cannot be made for the reason that the microarray has caused degradation or a nucleic acid amplification reaction has not sufficiently proceeded or the specimen has not been infected with a virus. In that case, the fluorescence of the detection spots needs not to be measured.

Accordingly, the present invention can be used in the cases where the presence or absence of a measurement target is checked, such as a test for tick/mold, a test of a microbe present in food and environment and a test of bacterial and viral infection to a human body.

In the present invention, after a fluorescent labeled target polynucleotide is brought into contact with the above microarray to carry out a hybridization reaction and an unreacted target polynucleotide is removed by washing, first, the fluorescence of a reference spot is measured. In the present invention, in addition to the fluorescent labeled target polynucleotide, a fluorescent labeled marker polynucleotide capable of hybridizing with any of the probe polynucleotides immobilized in the detection spots may be brought into contact with the microarray. The marker polynucleotide refers to a fluorescent labeled marker polynucleotide, which is capable of hybridizing with any of the probe polynucleotides immobilized in the detection spots usually in the stringent conditions.

The stringent conditions, which refer to the conditions in which a specific hybrid is formed and a non-specific hybrid is not formed, include low stringent conditions and high stringent conditions; however, the high stringent conditions are preferred. The low stringent conditions refer to conditions, for example, the washing after hybridization is performed in the conditions of 42° C., with 5×SSC, 0.1% SDS and preferably 50° C., 5×SSC, 0.1% SDS. The high stringent conditions refer to conditions, for example, the washing after hybridization is performed in the conditions of 65° C., with 0.1×SSC and 0.1% SDS. Under such stringent conditions, a polynucleotide consisting of a nucleotide sequence having a high homology (homology of 80% or more, preferably 90% or more, more preferably 95% or more, more preferably 98% or more) with a polynucleotide complementary to any of the probe polynucleotides can be hybridized.

As described above, the marker polynucleotide is designed such that it hybridizes with any of the probe polynucleotides immobilized in a reference spot. In addition, since the marker polynucleotide has a fluorescent label, even if a target polynucleotide does not hybridize with a probe, fluorescence should be detected in the reference spot. The fact that fluorescence is not detected or a fluorescence value is low means that a probe polynucleotide has been removed from the reference spot of the microarray. This also means that the probe polynucleotides in the detections spot have also been removed or otherwise, that a hybridization reaction has failed. Accordingly, by measuring the fluorescence of a reference spot and determining whether the fluorescence satisfies a predetermined value or not, whether the microarray has deteriorated or not can be determined, in other words, the reliability of the microarray can be determined. Furthermore, the reliability of a hybridization reaction can be determined.

The fluorescent label of a marker polynucleotide used herein is not particularly limited; however, it is preferable to use the same fluorescent label as used for a target polynucleotide. If the same fluorescent label is used, both fluorescent labels can be simultaneously measured by the same detector and measurement can be quickly and simply carried out.

In the microarray used in the present invention, preferably spots of probe polynucleotides (detection spots) and reference spots are aligned and preferably arranged in the form of a lattice. In addition, it is preferable that at least two reference spots are present. Regarding that a line connecting any two of the reference spots as a base line, the position of a detection spot (the center of the spot) is detected based on the distance from the reference spots and the angle with the base line. More specifically, based on the distance from the reference spots and the angle with the base line (angle between the base line and a line connecting between each detection spot and a reference spot), the center position of each spot can be determined. If desired, the center position of each spot can be determined based on a spot pitch.

Furthermore, the detection spots and the reference spots are aligned in the form of a lattice whose outer periphery forms a square or a rectangle and two reference spots are present at apexes on a diagonal line, which face each other. In this case, the intersection point at which two linear lines passing through the respective reference spots intersect at right angles is detected, and two connection lines connecting the intersection point and the respective two reference spots are detected. The length of a connection line is calculated and this distance is divided by a predetermined number (the number of spots on the outer periphery of the tetragon −1) to obtain the interval between the spots on the connection line. Based on the spot interval, the positions of individual spots can be detected. For example, if a microarray with a spot having 4 columns×4 rows is used, the number of spots on a connection line is 4. Provided that the length of the connection line is 900 μm, 900÷(4−1)=300. The spot interval becomes 300 μm. Using this, the point apart from the reference spot along the connection line by 300 μm can be defined as the center of a spot. The position further apart from this center along the connection line by 300 μm is the center of the next spot.

The two reference spots constituting the base line are preferably present at distant positions in the spots aligned on the microarray. The detection spots and the reference spots are arranged in the form of a lattice whose outer periphery forms a tetragon and the reference spots are preferably present at different apexes of the tetragon.

As a detector for measuring fluorescence of detection spots and reference spots, for example, a fluorescence laser microscope, a cooled CCD camera and a fluorescence scanning apparatus coupled with a computer are used and the intensity of fluorescence on the microarray can be automatically measured. A laser of a confocal type or a non-focal type may be used in place of the CCD camera. In this manner, image data can be obtained. Based on the data thus obtained, a target polynucleotide having a complementarity to a probe polynucleotide immobilized on a microarray can be identified. Based on this, a gene expression profile can be formed and the nucleotide sequence of a polynucleotide can be determined.

The microarray used in the present invention is prepared by immobilizing probe polynucleotides or mixtures of the probe polynucleotides on a carrier. As a material for the carrier, materials known in the art can be used. The material is not particularly limited. Examples thereof include precious metals such as platinum, platinum black, gold, palladium, rhodium, silver, mercury, tungsten and compounds of these and conductive materials such as a carbon material represented by graphite and carbon fiber; a silicon material such as single crystal silicon, amorphous silicon, silicon carbide, silicon oxide and silicon nitride and a composite material of these silicon materials such as SOI (silicon on insulator); inorganic materials such as glass, quartz glass, alumina, sapphire, ceramics, forsterite and photosensitive glass; and organic materials such as polyethylene, ethylene, polypropylene, cyclic polyolefin, polyisobutylene, polyethylene terephthalate, unsaturated polyester, a fluorine containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenolic resin, urea resin, epoxy resin, melamine resin, a styrene acrylonitrile co-polymer, an acrylonitrile styrene-butadiene co-polymer, a polyphenylene oxide and polysulfone. Although the shape of the carrier is not particularly limited, it is preferably planar.

As the carrier, a carrier having a carbon layer and a chemical modification group on the surface is preferably used. Examples of the carrier having a carbon layer and a chemical modification group on the surface include a carrier having a carbon layer and a chemical modification group on the surface of the substrate and a carrier having a chemical modification group on the surface of a substrate formed of a carbon layer. As the material for the substrate, materials known in the art can be used and are not particularly limited. The same materials mentioned above as the carrier material can be used.

A carrier having a fine planar structure is preferably used. The shape may be a rectangular, a square and a round. Although the shape is not limited, usually, a shape having 1 to 75 mm square, preferably 1 to 10 mm square, and more preferably 3 to 5 mm square, is used. Since a carrier having a fine planar structure is easily produced, substrates consisting of a silicon material and a resin material are preferably used. In particular, a carrier having a carbon layer and a chemical modification group on the surface of a substrate consisting of a single crystal silicon is more preferable. The single crystal silicon includes a single crystal silicon (sometimes referred to as a mosaic crystal) in which crystalline axis slightly varies part by part and a single crystal silicon containing a disturbance at an atomic level (lattice defect).

The carbon layer to be formed on a substrate is not particularly limited; however, any of the synthesized diamond, high-pressure synthesized diamond, naturally occurring diamond, soft diamond (for example, diamond like carbon), amorphous carbon, a carbonaceous substance (for example, graphite, fullerene, carbon nanotube), or a mixture of these or a laminate of these is preferably used. Furthermore, carbides such as hafnium carbide, niobium carbide, silicon carbide, tantalum carbide, thorium carbide, titanium carbide, uranium carbide, tungsten carbide, zirconium carbide, molybdenum carbide, chrome carbide and vanadium carbide may be used. The soft diamond used herein is a general term referring to an incomplete diamond construct, which is a mixture of diamond and carbon, called diamond like carbon (DLC) and the mixing ratio thereof is not particularly limited.

The carbon layer can be formed by a known method. Examples of the method include a micro-wave plasma CVD (chemical vapor deposit) method, an ECRCVD (Electric cyclotron resonance chemical vapor deposit) method, an ICP (Inductive coupled plasma) method, a direct current sputtering method, an ECR (Electric cyclotron resonance) sputtering method, an ionization vapor deposition method, an arc-style vapor deposition method, a laser vapor deposition method, an EB (Electron beam) vapor deposition method and a resistance heating vapor deposition method.

When a carbon layer is formed on the surface of a substrate, the thickness of the carbon layer is usually, a single layer to about 100 μm. If the layer is extremely thin, the surface of the underlying substrate may be locally exposed. On the other hand, if the layer is extremely thick, productivity decreases. Thus, the thickness is preferably 2 nm to 1 μm and more preferably 5 nm to 500 nm.

By introducing a chemical modification group into the surface of a substrate having the carbon layer formed thereon, an oligonucleotide probe can be strongly immobilized to a carrier. The chemical modification group to be introduced, which is appropriately selected by those skilled in the art, is not particularly limited. Examples thereof include an amino group, a carboxyl group, an epoxy group, a formyl group, a hydroxyl group and an active ester group.

Introduction of an amino group can be carried out, for example, by irradiating the carbon layer with UV rays or by treating it with a plasma in ammonia gas; or by irradiating the carbon layer with UV rays in chlorine gas for chlorination and further irradiating it with UV rays in ammonia gas; or by reacting a gas of polyvalent amine such as methylene diamine and ethylene diamine with a chlorinated carbon layer.

Introduction of a carboxyl group can be carried out, for example, by reacting an appropriate compound with a carbon layer aminated as mentioned above. Examples of the compound to be used for introducing a carboxyl group include halocarboxylic acids represented by Formula: X—$R^1$—COOH (in the formula, X represents a halogen atom and $R^1$ represents divalent hydrocarbon group having 10 to 12 carbon atoms) such as chloroacetic acid, fluoroacetic acid, bromoacetic acid, iodoacetic acid, 2-chloropropionic acid, 3-chloropropionic acid, 3-chloroacrylic acid and 4-chlorobenzoic acid; dicarboxylic acids represented by Formula: HOOC—$R^2$—COOH (in the formula, $R^2$ represents a single bond or a divalent hydrocarbon group having 1 to 12 carbon atoms) such as oxalic acid, malonic acid, succinic acid, maleic acid, fumaric acid and phthalic acid; polyvalent carboxylic acids such as polyacrylic acid, polymethacrylic acid, trimellitic acid and butanetetracarboxylic acid; keto acid or aldehyde acid represented by Formula: $R^3$—CO—$R^4$—COOH (in the formula, $R^3$ represents a hydrogen atom or a divalent hydrocarbon group having 1 to 12 carbon atoms and $R^4$ represents a divalent hydrocarbon group having 1 to 12 carbon atoms); dicarboxylic acid monohalides represented by Formula: X—OC—$R^5$—COOH (in the formula, X represents a halogen atom and $R^5$ represents a single bond or a divalent hydrocarbon group having 1 to 12 carbon atoms) such as succinic acid monochloride, malonic acid monochloride; and acid anhydrides such as phthalic anhydrite, succinic anhydride, oxalic anhydride, maleic anhydride and butanetetracarboxylic anhydride.

Introduction of an epoxy group can be carried out, for example, by reacting an appropriate polyvalent epoxy compound with a carbon layer aminated as described above or by reacting an organic peroxide with carbon=carbon double bond contained in the carbon layer. Examples of organic peroxide include peracetic acid, perbenzoic acid, diperoxyphthalic acid, performic acid and trifluoroperacetic acid.

Introduction of a formyl group can be carried out, for example, by reacting glutaraldehyde with a carbon layer aminated as described above.

Introduction of a hydroxyl group can be carried out, for example, by reacting water with a carbon layer chlorinated as mentioned above.

The active ester group refers to an ester group having highly acidic electron-attracting group in the alcohol moiety of an ester group, thereby activating a nucleophilic reaction, in short, a highly reactive ester group. This is an ester group having an electron-attracting group in the alcohol moiety of an ester group and activated more than an alkyl ester. The active ester group has reactivity to groups such as an amino group, a thiol group and a hydroxy group. Further more specifically, e.g., a phenolic ester, a thiophenol ester, a N-hydroxyamine ester, cyanomethyl ester and an ester of a heterocyclic hydroxy compound are known as an active ester group having further higher activity than an alkyl ester, etc. More specific examples of the active ester group include a p-nitrophenyl group, a N-hydroxysuccinimide group, a succinic acid imide group, a phthalic acid imide group and a 5-norbornene-2,3-dicarboxyimide group. In Particular, a N-hydroxysuccinimide group is preferably used.

Introduction of the active ester group can be carried out, for example, by converting a carboxyl group introduced as described above into an active ester group with a dehydration condensing agent, such as cyanamide or carbodiimide (for example, 1-[3-(dimethylamino)propyl]-3-ethylcarbodiimide), and a compound such as N-hydroxysuccinimide. By virtue of the treatment, a group in which an active ester group such as a N-hydroxy succinimide group is bound to an end of a hydrocarbon group via an amide bond (JP Patent Publication (Kokai) No. 2001-139532A) can be formed.

Probe polynucleotides and probe polynucleotide mixtures are separately dissolved in spotting buffers to prepare spotting solutions. Each of the solutions is dispensed to a 96-well or 384-well plastic plate. The dispensed solution is spotted on a carrier by a spotter apparatus, etc. to produce a microarray. Alternatively, the spotting solution may be manually spotted by a micropipetter.

After spotting, to cause the binding reaction of each of the probe polynucleotides and the probe polynucleotide mixtures with a carrier to proceed, incubation is preferably performed. The incubation is performed usually at a temperature of -20 to 100° C. and preferably 0 to 90° C., usually for 0.5 to 16 hours and preferably 1 to 2 hours. The incubation is desirably performed under an atmosphere of high-humidity, for example, a humidity of 50 to 90%. Following the incubation, to remove DNA not bound to a carrier, washing with a washing liquid (for example, 50 mM TBS/0.05% Tween20, 2×SSC/0.2% SDS solution, ultrapure water) is preferably performed.

In an embodiment of the present invention, after the step of removing an unreacted target polynucleotide by washing a microarray, before actual measurement, in other words, measurement of fluorescence at individual detection spots in which probe polynucleotides are immobilized, the following steps are further preferably performed. The following steps may be performed before or after fluorescence is measured at a reference spot.

A step of obtaining a plurality of background values by measuring brightness of a position at a predetermine distance apart from the center of a spot, with respect to a plurality of spots, a step of calculating a background representative value representing a plurality of background values thus obtained, and a step of calculating a difference between the background value of each of all spots or all spots for which a background value is measured and the background representative value, and determining that measurement cannot be made if a spot having a difference of a predetermined value or more is present.

In the spots herein, detection spots and reference spots are both included. As a plurality of spots from which background values are obtained, at least all spots forming the outer periphery of the spots aligned in a microarray are preferably used. Furthermore, although it is not necessary to measure a background value with respect to all spots, background values of all spots may be measured. A plurality of spots for measuring a background value, for example, in the case where detection spots and reference spots are arranged in the form of a lattice whose outer periphery forms a tetragon, are usually, at least 2 spots corresponding the apexes of the tetragon, preferably at least 4 spots corresponding the apexes of the tetragon, and more preferably, all spots in the outermost periphery. More specifically, in the case where 16 columns×16 rows spots are present, 60 spots arranged in the outermost periphery or all spots (256 spots) are used.

When brightness is measured at a position within a predetermined range from the center of a spot and employed as a background value, the predetermined range from the center is appropriately set based on the size of the spot and intervals of spots. For example, the predetermined range can be defined as the range at a predetermined distance or more apart from the center of a spot and within a tetragon having a side having a length equal to the interval between spots and having a common center with the spot. For example, the predetermined range is the range at a distance of 70 μm or more apart from the spot center and within a tetragon of 1000 μm square, and preferably the range at a distance of 70 μm or more apart from the spot center and within a tetragon of 380 μm square. Furthermore, the average of measured brightness values of all or part of spots within a predetermined range may be used as the background value or measured brightness of a single spot within the predetermined range may be used as the background value.

A method of determining the center position of a spot is not particularly limited. For example, a portion having a predetermined fluorescence intensity (for example, 3000 or more) is detected in each spot and the portion can be used as the center of the spot. Alternatively, the center position may be determined by assuming the line connecting the centers of two reference spots as a base line and determining the center position of each spot based on e.g., the distance from the reference spots and the angle with the base line and the spot pitch.

The background representative value, although it is not particularly limited as long as it represents a plurality of measured background values, is preferably an average or median of a plurality of background values.

With respect to all spots or all spots whose background values are measured, difference between each of the background values and the background representative value is calculated. If a spot having a difference of a predetermined value or more is present, it can be determined that the background values around the spot significantly vary. Accordingly, it is determined that the microarray is insufficiently washed and lacks reliability and thus measurement cannot be made. Herein, although the predetermined value varies depending upon the conditions, for example, when an image is displayed with 16 bit harmony, the predetermined value can be set to be 1000 or more. If an image is displayed, for example, with 8 bit harmony, the predetermined value can be set to be less than 50.

In another embodiment of the present invention, after the step of removing an unreacted target polynucleotide by washing a microarray, before actual measurement, in other words, measurement of fluorescence at individual detection spots in which probe polynucleotides are immobilized, the following steps are further preferably performed. The following steps may be carried out before or after fluorescence measurement at a reference spot.

A step of obtaining a plurality of background values by measuring brightness of a position at a predetermine distance apart from the center of a spot, with respect to a plurality of spots, a step of calculating an average or median of a plurality of background values as a background representative value, a step of determining that measurement cannot be made, if the background representative value is a predetermined value or more.

In the spots herein, detection spots and reference spots are both included. As a plurality of spots from which background values are obtained, at least all spots forming the outer periphery of the spots aligned in a microarray are preferably used. Furthermore, although it is not necessary to measure a background value with respect to all spots, background values of all spots may be measured. A plurality of spots for measuring a background value, for example, in the case where detection spots and reference spots are arranged in the form of a lattice whose outer periphery forms a tetragon, are usually, at least 2 spots corresponding the apexes of the tetragon, preferably at least 4 spots corresponding the apexes of the tetragon, and more preferably, all spots in the outermost periphery. More specifically, in the case where 16 columns×16 rows spots are present, 60 spots arranged in the outermost periphery or all spots (256 spots) are used.

The predetermined distance from the center of a spot and a method of determining the center are the same as mentioned above.

If the background representative value, which is an average or median of a plurality of background values, is a predetermined value or more, it can be determined that the background values around the spot are large as a whole. Accordingly, it is determined that the microarray is insufficiently washed and lacks reliability and thus, measurement cannot be made. Herein, although the predetermined value varies depending upon the conditions, however, for example, in the case of 16 bits, the predetermined value can be set to be 1000 or more.

The present invention further relates to a kit for detecting the hybridization between a probe polynucleotide and a target polynucleotide as mentioned above. The kit of the present invention has a microarray having not only a plurality of detection spots in which a plurality of types of probe polynucleotides are each immobilized but also at least one reference spot in which all types of probe polynucleotides immobilized in the detection spots are immobilized; and a fluorescent labeled marker polynucleotide capable of hybridizing with any of the probe polynucleotides immobilized in the detection spots. The probe polynucleotide, target polynucleotide, probe polynucleotide mixture, microarray and marker polynucleotide, etc. are the same as mentioned above. The kit of the present invention may further include a hybridization buffer, a washing buffer, a micro plate and a nylon membrane.

The present invention will be more specifically described by way of Examples below. The technical scope of the present invention should not be limited to the following Examples.

EXAMPLES

Example 1 Preparation of Carrier

To a silicon substrate of 3 mm square, two DLC layers were formed by using an ionic vapor deposition method in the following conditions.

TABLE 1

| | | First layer | Second layer | |
|---|---|---|---|---|
| Raw material gas | $CH_4$ | 4.75 | 47.5 | (sscm) |
| | $H_2$ | 0.25 | 2.5 | (sscm) |
| Operation pressure | | 3.0 | 8.0 | (Pa) |
| Substrate bias | Direct current voltage | 500 | 500 | (V) |
| | High frequency power | 100 | — | (W) |
| Anode voltage | | 50 | 50 | (V) |
| Filament | Voltage | 7 | 7 | (V) |
| | Current | 22 | 22 | (A) |

On the resultant silicon substrate having DLC layers on the surface, an amino group was introduced by using ammonia plasma in the following conditions.

TABLE 2

| Raw material gas | $NH_3$ | 30 | (sscm) |
|---|---|---|---|
| Operation pressure | | 8.0 | (sscm) |
| Substrate bias | Direct current voltage | 500 | (Pa) |
| | High frequency power | — | (W) |
| Anode voltage | | 50 | (V) |
| Filament | Voltage | 7 | (V) |
| | Current | 22 | (A) |

The substrate was soaked in a 1-methyl-2-pyrrolidone solution containing 140 mM succinic anhydride and 0.1M sodium borate, for 30 minutes to introduce a carboxyl group. The substrate was soaked in a solution containing 0.1M potassium phosphate buffer, 0.1M 1-[3-(dimethylamino)propyl]-3-ethyl carbodiimide and 20 mM N-hydroxysuccinimide, for 30 minutes to induce activation. Consequently, a carrier having DLC layers and a chemical modification group, i.e., N-hydroxysuccinimide group, on the surface of the silicon substrate was obtained.

Example 2 Preparation of Microarray

Four types of probe DNAs (probe polynucleotides) for ABO blood type determination and mixtures of four types of probe DNAs for the blood type determination were separately dissolved in a Sol. 6 and spotted (SPBIO manufactured by Hitachi Software Engineering Co., Ltd.) on the carrier prepared in Example 1 in accordance with the arrangement shown in FIG. 1. More specifically, the probe DNAs were spotted in detection spots, whereas the probe DNA mixtures were spotted in reference spots. Four types of probe DNAs were each dissolved so as to obtain a concentration of 10 μM and separately spotted. The probe DNA mixture was prepared by mixing and dissolving four types of probe DNAs in an equivalent amount so as to have a concentration of 2.5 μM, 5 μM, 10 μM, 20 μM, or 40 μM in total and then spotted. For example, a spot of a probe DNA mixture (40 μM) was obtained by spotting a solution containing four types of probe DNAs each in an amount of 10 μM for each is spotted. The pitches of the spots were set to be 280 μm.

The DNA sequences of four types of probes for blood type determination are as follows:

```
AB type probe:
                                    (SEQ ID NO: 1)
5'-TCCTCGTGGTGACCCCTTGG-3'

O type probe:
                                    (SEQ ID NO: 2)
5'-TCCTCGTGGTACCCCTTGGC-3'

AO type probe:
                                    (SEQ ID NO: 3)
5'-ACAAGTACCTGCTGCGCCAC-3'

B type probe:
                                    (SEQ ID NO: 4)
5'-ACAAGTACCTACTGCGCCAC-3'
```

Based on the value (O type/AB type) of nucleic acids hybridized with O type probe to nucleic acids hybridized with AB type probe, whether the blood type of subject is OO type, ?O type or ?? type (?=A or B) can be determined. The ?O type refers to AO type or BO type; whereas the ?? type refers to AA type, AB type or BB type. The value of O type/AB type decreases in the order of OO type>?O type>?? type. Accordingly, if a threshold value of O type/AB type is set, whether the blood type of subject is OO type, ?O type or ?? type can be determined. For example, if the value of O type/AB type is 3.0 or more, the blood type is determined as OO type. If the value of O type/AB type is 1.0 or more and less than 3.0, the blood type is determined as ?O type. If the value of O type/AB type is less than 1.0, the blood type can be determined as ?? type.

Based on the value (B type/AO type) of nucleic acids hybridized with B type probe to nucleic acids hybridized with AO type probe, whether the blood type of subject is BB type, B? type or ?? type (?=A or O) can be determined. The B? type refers to AB type or BO type, whereas the ?? type refers to AA type, AO type or OO type. The value of B type/AO type is such that BB type>B? type>?? type. Accordingly, if a threshold value of B type/AO type is set, whether the blood type of subject is BB type, B? type or ?? type can be determined. For example, if the value of B type/AO type is 3.0 or more, the blood type is determined as BB type. If the value of B type/AO type is 1.0 or more and less than 3.0, the blood type is determined as B? type. If the value of B type/AO type is less than 1.0, the blood type can be determined as ?? type.

After baking was performed at 80° C. for 1 hour, the substrate was washed in 2×SSC/0.2% SDS at room temperature for 15 minutes while stirring and at 70° C. for 5 minutes, subsequently washed with ultrapure water and centrifugally dried to prepare a microarray having probe DNAs and probe DNA mixtures spotted thereon.

Example 3 Hybridization with Target DNA (1) Blast cells were taken from the cheeks of subjects having the AO blood type and BO blood type and nucleic acids were extracted (QIAamp, manufactured by QIAGEN). The regions (ABO glycosyl transferase gene) hybridizing with the probe DNAs were amplified by PCR using the following primer sets (GeneAmp9700, manufactured by ABI).

```
Forward primer 1:
                                  (SEQ ID NO: 5)
5'-AGCTCAGCTTGCTGTGTGTT-3'

Reverse primer 1:
                                  (SEQ ID NO: 6)
5'-AGATGCTGCATGAATGACC-3'

Forward primer 2:
                                  (SEQ ID NO: 7)
5'-GCCTGCCTTGCAGATACGTG-3'

Reverse primer 2:
                                  (SEQ ID NO: 8)
5'-CAGAGTTTACCCGTTCTGCT-3'
```

CyDye (Cy5) was used as a label. The composition of a PCR solution and PCR conditions were as follows.

TABLE 3

| Composition of PCR solution: | |
|---|---|
| Fw primer 1 (10 µM) | 0.5 µL |
| Rv primer 1 (10 µM) | 0.5 µL |
| Fw primer 2 (10 µM) | 0.5 µL |
| Rv primer 2 (10 µM) | 0.5 µL |
| PCR Buffer | 2 µL |
| dNTP (concentration of dCTP is 1/10) | 2 µL |
| Cy5-dCTP | 0.5 µL |
| Template DNA | 1 µL |
| Ex Taq | 0.1 µL |
| H₂O | 13 µL |
| total | 20.6 µL |

TABLE 4

| PCR conditions | | |
|---|---|---|
| 95° C. | 5 min | |
| 95° C. | 10 sec | |
| 60° C. | 10 sec | } 45 cycles |
| 72° C. | 20 sec | |
| 72° C. | 5 min | |
| 4° C. | ∞ | |

(2) To a hybridize buffer (3×SSC/0.3% SDS)(1 µL), a PCR product (2 µL) was mixed. The resultant mixture was delivered by drops to the microarray prepared in Example 2. Hybridization was performed at 55° C. for 1 hour. The microarray was washed with 2×SSC/0.2% SDS (shaken 10 times) and subsequently washed with 2×SSC (shaken 10 times).

Figure 2:
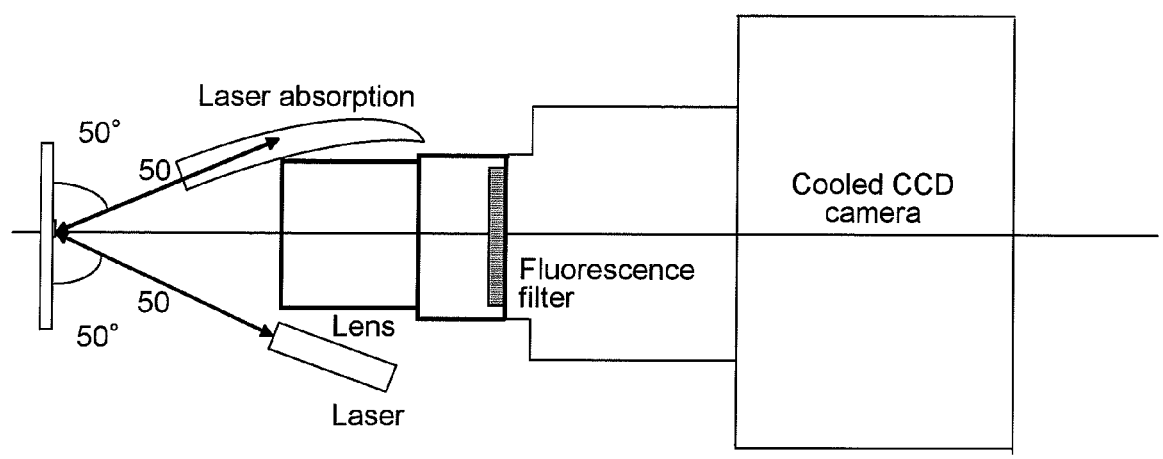
FIG. 2 shows an embodiment of a detector for detecting fluorescence of a microarray.

(4) Fluorescence was measured by using the detector shown in FIG. 2. The whole surface of the microarray was irradiated with Red laser used as excitation light (exposure time: 15 seconds). Light having wavelengths except a desired wavelength is cut through a fluorescence filter.

Figure 3:
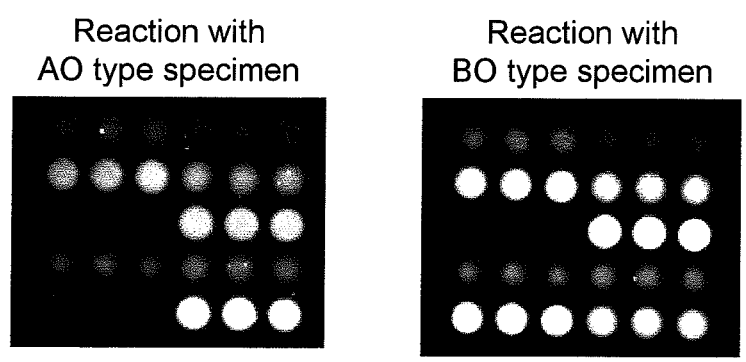
FIG. 3 shows images of fluorescence measured after a hybridization reaction in a microarray.
Figure 4:
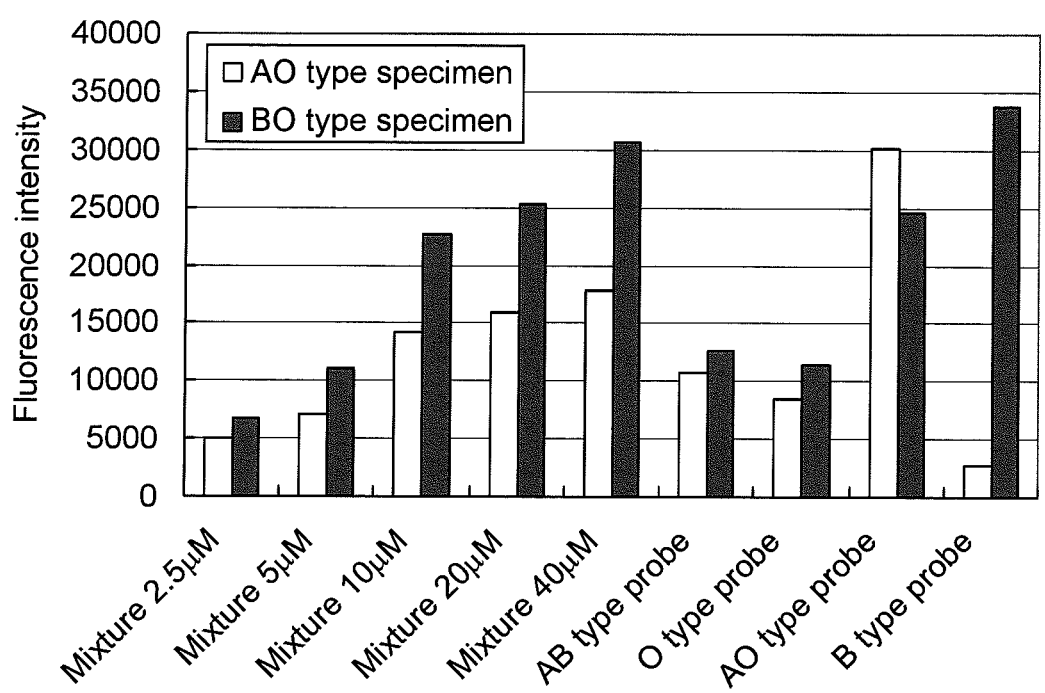
FIG. 4 shows the results of fluorescence intensity measured after a hybridization reaction in a microarray.

FIG. 3 shows a fluorescence image measured after hybridization. A median of numeral values of pixels within a diameter of φ100 µm from the center of a spot was calculated as a representative value. The results are shown in the following Table 5 and FIG. 4.

TABLE 5

| | Blood type of specimen | |
|---|---|---|
| Spot | AO type | BO type |
| Probe mixture 2.5 µM | 5064 | 6817 |
| Probe mixture 5 µM | 7140 | 11143 |
| Probe mixture 10 µM | 14171 | 22732 |
| Probe mixture 20 µM | 15874 | 25220 |
| Probe mixture 40 µM | 17862 | 30689 |
| AB type probe | 10702 | 12671 |
| O type probe | 8431 | 11472 |
| AO type probe | 30129 | 24656 |
| B type probe | 2758 | 33694 |

From the above results, it was demonstrated that even if a probe mixture containing all probe DNAs immobilized in detection spots is spotted onto the same microarray on which detection spots are formed, a fluorescence signal can be detected in the detection spots without problem and a fluorescence signal can also be detected in a reference spot.

Example 4

Figure 5:
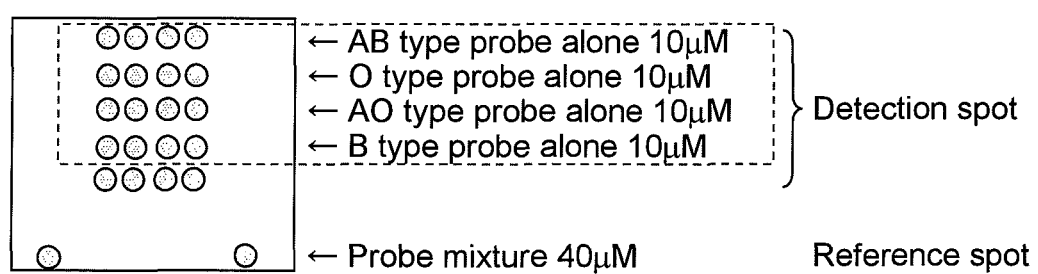
FIG. 5 shows an embodiment of arrangement of probe DNA spots (detection spots) and probe DNA mixture spots (reference spots) in a microarray.

In the same procedure as in Example 2, four types of probe DNAs (probe polynucleotides) for ABO blood type determination and mixtures of four types of probe DNAs for the blood type determination were spotted onto the carrier prepared in Example 1 in accordance with the arrangement shown in FIG. 5 to prepare a microarray. Furthermore, a microarray having a blank reference spot (shown in FIG. 5) was also prepared as a conventional microarray.

Figure 6:
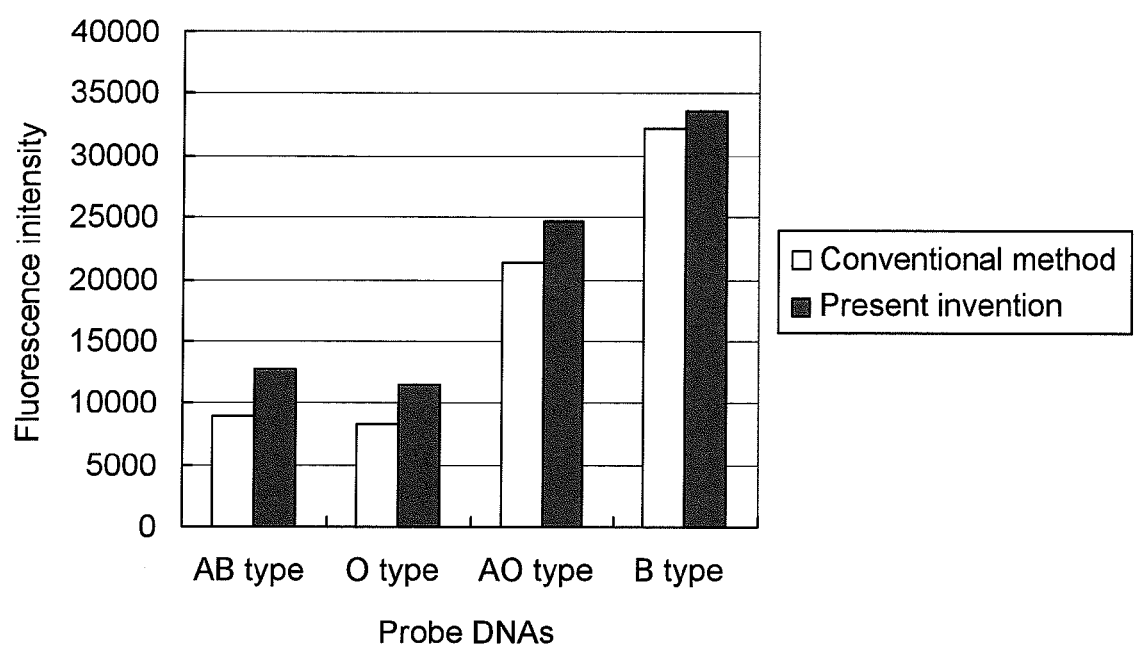
FIG. 6 shows the fluorescence measurement results obtained by hybridizing a target DNA derived from a specimen with two types of microarrays (conventional method and the present invention).

In the same procedure as in Example 3, target DNAs derived from an AO type specimen and a BO type specimen were brought into contact with two types of microarrays and fluorescence intensity was measured. The results are shown in FIG. 6. When the case of using a microarray according to a conventional method is compared to the microarray according to the present invention, no substantial difference was observed in fluorescence intensity of each detection spot. In addition, no substantial difference was observed in a values calculated from fluorescence intensity for determining a blood type, i.e., a value of fluorescence intensity in the spot of an O type probe relative to fluorescence intensity in the spot of AB type probe, and a value of fluorescence intensity in the spot of a B type probe relative to fluorescence intensity in the spot of AO type.

From the above, it was demonstrated that even if a probe mixture containing all probe DNAs immobilized in detection spots is spotted onto the same microarray on which detection spots are formed, the fluorescence intensity obtained at the detection spots is not affected.

Example 5

Figure 7:
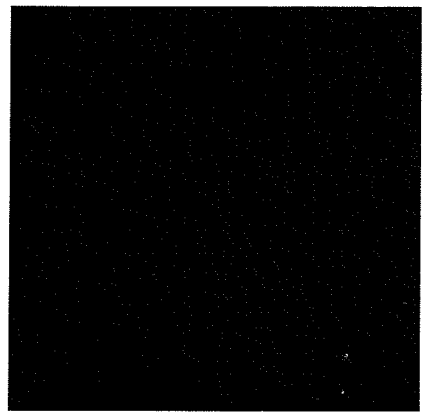
FIG. 7 shows a fluorescence image obtained by carrying out PCR of a nucleic acid extracted from a specimen without using a primer and delivering the resultant PCR product by drops onto a microarray.

In Example 3, a nucleic acid extracted from a BO type specimen was subjected to PCR without adding a primer. The resultant PCR product was delivered by drops to a microarray prepared by spotting four types of probe DNAs (probe polynucleotides) for ABO blood type determination and mixtures of four types of probe DNAs for the blood type determination onto the carrier prepared in Example 1 in accordance with the arrangement shown in FIG. 5. Subsequently, hybridization and fluorescence measurement were carried out in the same procedure as in Example 3 except the above. The obtained fluorescence images are shown in FIG. 7.

From the above, it was demonstrated that in the case where PCR is not normally performed, no fluorescence is detected not only in the detection spots but also in the reference spots in which probe DNA mixtures are immobilized and thus PCR failure can be determined. More specifically, when fluorescence of a reference spot in which a probe mixture is immobilized is measured and if fluorescence is detected, detection of fluorescence indicates that a nucleic acid amplification reaction is sufficiently carried out and whether measurement can be performed or not can be automatically determined on software without checking an image.

Example 6 Preparation of Microarray

Figure 8:
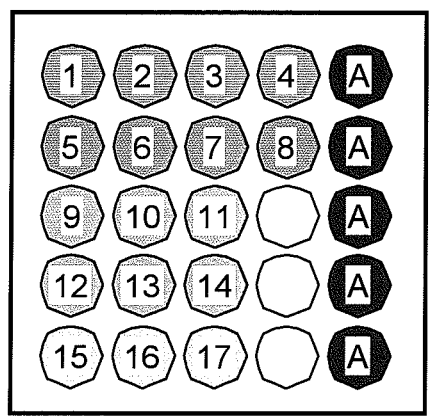
FIG. 8 shows an embodiment of arrangement of probe DNA spots (detection spots) and probe DNA mixture spots (reference spots) in a microarray. Spots 1 to 17 are detection spots and spots A are reference spots.

Probe DNAs (17 types) for determining the genome type of BK virus (genome type of VP1 gene of BK virus) transmitted to a subject and a mixture of the 17 types probe DNAs were each dissolved in Sol. 6 and spotted (SPBIO manufactured by Hitachi Software Engineering Co., Ltd.) on the carrier prepared in Example 1 in accordance with the arrangement shown in FIG. 8. More specifically, probe DNAs were spotted in detection spots 1 to 17 and the probe DNA mixture was spotted in reference spots A. 17 types of probe DNAs were each dissolved such that each had a concentration of 5 µM and spotted. The probe DNA mixture was prepared by mixing and dissolving 17 types of probes in an equivalent amount so as to obtain a concentration of 85 µM in total and then spotted. The pitches of spots were set to be 280 µm.

Sequences of 17 types of probe DNAs are as follows:

TABLE 6

| Spot position | Probe DNA sequence | SEQ ID NO. |
| --- | --- | --- |
| 1 | 5'-CCCAATTTAAATGAGGACC-3' | 9 |
| 2 | 5'-CCCAATTTGAATGAGGACC-3' | 10 |
| 3 | 5'-CCCAACCTAAATGAGGACC-3' | 11 |
| 4 | 5'-CCTAATTTGAATGAGGATC-3' | 12 |

TABLE 6-continued

| Spot position | Probe DNA sequence | SEQ ID NO. |
| --- | --- | --- |
| 5 | 5'-GCTGTAACTGTACAAACAGA-3' | 13 |
| 6 | 5'-GCTGTAACAGTACAAACAGA-3' | 14 |
| 7 | 5'-GCTGTAACTGTAAAAACAGA-3' | 15 |
| 8 | 5'-GCTGTGACTGTAAAAACAGA-3' | 16 |
| 9 | 5'-AACAGAGGTTATTGGAATAA-3' | 17 |
| 10 | 5'-AACAGAGGTCATTGGAATAA-3' | 18 |
| 11 | 5'-AACAGAGGITATGGGAATAA-3' | 19 |
| 12 | 5'-CTGGGGTAGATGCTATTACA-3' | 20 |
| 13 | 5'-CTGGGGTAGATGCTATAACA-3' | 21 |
| 14 | 5'-CTGGGCTAGATGCTATAACA-3' | 22 |
| 15 | 5'-ATGCTTCCTAAACCCAGAAA-3' | 23 |
| 16 | 5'-ATGCTTTCTAAACCCAGAAA-3' | 24 |
| 17 | 5'-ATGCTTTCTAAATCCAGAAA-3' | 25 |
| A | Probe DNA mixture | — |

After baking was performed at 80° C. for 1 hour, the substrate was washed in 2×SSC/0.2% SDS at room temperature for 15 minutes while stirring and at 70° C. for 5 minutes, subsequently washed with ultrapure water and centrifugally dried to prepare a microarray having probe DNAs and probe DNA mixtures spotted thereon.

Example 7 Hybridization of Target DNA (1) From urine specimens of three human subjects, nucleic acids were extracted (QIA, manufactured by QIAGEN). The regions (VP1 gene of BK virus) hybridized with the probe DNAs were amplified by PCR using the following primer set (GeneAmp9700, manufactured by ABI).

Forward primer:
(SEQ ID NO: 26)
5'-CAAGTGCCAAAACTACTAAT-3'

Reverse primer:
(SEQ ID NO: 27)
5'-TGCATGAAGGTTAAGCATGC-3'

CyDye (Cy5) was used as a label. The composition of a PCR solution and PCR conditions are as follows.

TABLE 7

| Composition of PCR solution: | |
| --- | --- |
| Fw primer 1 (10 µM) | 0.5 µL |
| Rv primer 1 (10 µM) | 0.5 µL |
| PCR Buffer | 2 µL |
| dNTP (concentration of dCTP is 1/10) | 2 µL |
| Cy5-dCTP | 0.5 µL |
| Template DNA | 1 µL |
| Ex Taq | 0.1 µL |
| $H_2O$ | 14 µL |
| total | 20.6 µL |

TABLE 8

| PCR conditions | | |
|---|---|---|
| 95° C. | 5 min | |
| 95° C. | 10 sec | |
| 58° C. | 30 sec | } 50 cycles |
| 72° C. | 30 sec | |
| 72° C. | 5 min | |
| 4° C. | ∞ | |

(2) To a hybridize buffer (3×SSC/0.3% SDS), a PCR product (2 μL) was mixed. The resultant mixture was delivered by drops to the microarray prepared in Example 6, and hybridization was performed at 55° C. for 1 hour. The microarray was washed with 2×SSC/0.2% SDS (shaken 10 times) and subsequently washed with 2×SSC (shaken 10 times).

Figure 9:
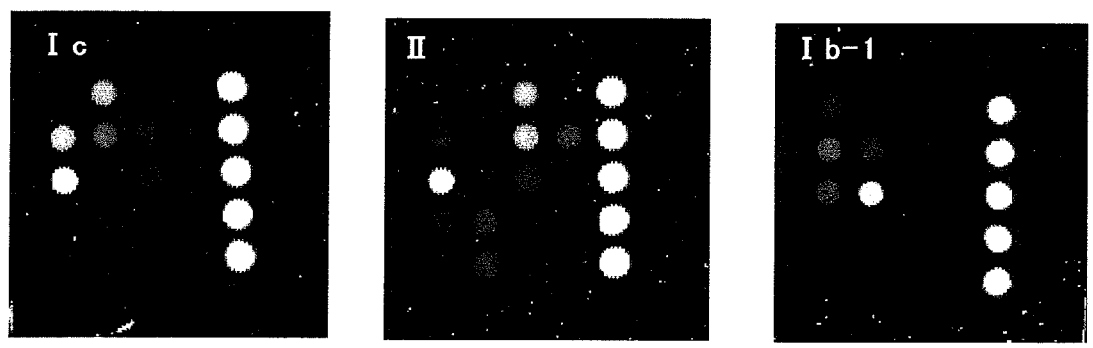
FIG. 9 shows fluorescence measurement results obtained by hybridizing a target DNA derived from a specimen with a microarray.

(4) Fluorescence measurement was performed by FLA8000 (Fuji Film Corporation). FIG. 9 shows fluorescence images measured after hybridization. As a result, three genome types of BK viruses could be detected for each of the three subjects. In addition, fluorescence was detected in reference spots.

From the above, it was demonstrated that even if 17 types of probe DNAs are immobilized in detection spots of a microarray and a mixture of 17 types of probe DNAs are immobilized in reference spots, fluorescence can be detected at the reference spots by hybridizing a target DNA derived from a specimen and whether measurement can be performed or not can be determined, and the positions of the detection spots can be determined based on the fluorescence of the reference spots.

All publications, patents and patent applications cited in the specification are incorporated in their entirety in the specification of the application by reference.

The invention claimed is:

1. A method of detecting hybridization between a probe polynucleotide and a target polynucleotide with a microarray comprising the steps of
   a) bringing a fluorescent labeled target polynucleotide into contact with a microarray having a plurality of detection spots in each of which one of a plurality of types of probe polynucleotides is immobilized and at least one reference spot in which at least two types of the probe polynucleotides immobilized in the detection spots are immobilized, and allowing the target polynucleotide to hybridize,
   b) removing any unhybridized target polynucleotide by washing the microarray,
   c) measuring fluorescence of the reference spot and determining that if a predetermined value is satisfied the hybridization is reliable, and
   d) measuring fluorescence of each of the detection spots if it is determined that hybridization is reliable.

2. The method according to claim 1, wherein all types of probe polynucleotides immobilized in the detection spots are immobilized in the reference spot.

3. The method according to claim 1, wherein the target polynucleotide to be brought into contact with the microarray contains a polynucleotide to be hybridized with the probe polynucleotides immobilized in the reference spot.

4. The method according to claim 1, wherein the detection spots and the reference spots are aligned in the microarray; at least two reference spots are present; and a line connecting any two of the reference spots is defined as a base line, positions of the detection spots are detected based on a distance from the reference spots and an angle with the base line.

5. The method according to claim 4, wherein the detection spots and the reference spots are arranged in the form of a lattice whose outer periphery forms a tetragon and the reference spots are present at different apexes of the tetragon.

6. The method according to claim 1, wherein the detection spots and the reference spots are aligned in the microarray in the form of a lattice whose outer periphery forms a square or a rectangle; the reference spots are present at two apexes of a diagonal line thereof; and
   an intersection point at which two linear lines passing through the reference spots intersect at right angles is detected, lengths of the two connection lines connecting the intersection point and the reference spots are detected to detect a position of each of the detection spots on a connection line based on a length of the connection line and the number of spots.

7. The method according to claim 1, further comprising the step of bringing a marker polynucleotide into contact with the microarray, wherein the marker polynucleotide has the same fluorescent label as the target polynucleotide and has a homology of 95% or more with a polynucleotide complementary to any of the probe polynucleotides immobilized in the detection spots.

8. A kit for detecting hybridization between a probe polynucleotide and a target polynucleotide, comprising
   a microarray having a plurality of detection spots in each of which one of a plurality of types of probe polynucleotides is immobilized and at least one reference spot in which at least two types of probe polynucleotides immobilized in the detection spots are immobilized; and a fluorescent labeled marker polynucleotide capable of hybridizing with any of the probe polynucleotides immobilized in the detection spots.

9. The kit according to claim 8, wherein all types of probe polynucleotides immobilized in the detection spots are immobilized in the reference spot.

* * * * *